(12) United States Patent
Cule et al.

(10) Patent No.: US 7,107,547 B2
(45) Date of Patent: Sep. 12, 2006

(54) METHOD OF GRAPHICALLY INDICATING PATIENT INFORMATION

(75) Inventors: LaVonne Cule, St. Clair, MO (US); Beth Frankenberg, Union, MO (US); Grady Smith, 1279 Roller Rd., St. Clair, MO (US) 63077

(73) Assignee: Grady Smith, St. Clair, MO (US)

( * ) Notice: Subject to any disclaimer, the term of this patent is extended or adjusted under 35 U.S.C. 154(b) by 695 days.

(21) Appl. No.: 09/870,373

(22) Filed: May 30, 2001
(Under 37 CFR 1.47)

(65) Prior Publication Data

US 2002/0055855 A1    May 9, 2002

Related U.S. Application Data

(60) Provisional application No. 60/208,334, filed on May 31, 2000.

(51) Int. Cl.
*G06Q 50/00* (2006.01)

(52) U.S. Cl. .............................. 715/810; 705/2; 705/3; 434/267

(58) Field of Classification Search ................ 345/706, 345/701, 702; 705/2–3; 367/116; 715/846, 715/706, 810; 434/267
See application file for complete search history.

(56) References Cited

U.S. PATENT DOCUMENTS

| | | |
|---|---|---|
| 1,962,687 A | 6/1934 | Hodge |
| 3,316,669 A | 5/1967 | Nachbar |
| 3,715,816 A | 2/1973 | White |
| 4,063,369 A | 12/1977 | Hart |
| 4,165,890 A | 8/1979 | Leff |
| 4,306,368 A | 12/1981 | Coghill et al. |
| 4,406,998 A | 9/1983 | Willough |
| 4,465,465 A | 8/1984 | Nelson |
| 4,650,423 A | 3/1987 | Sprague et al. |
| 4,656,603 A * | 4/1987 | Dunn .......................... 345/835 |
| 4,702,700 A | 10/1987 | Taylor |
| 4,761,633 A | 8/1988 | Leff et al. |
| 4,795,348 A | 1/1989 | Garthwaite |
| 4,863,386 A | 9/1989 | Maxey |
| 4,865,549 A | 9/1989 | Sonsteby |
| 4,915,632 A | 4/1990 | Leff et al. |
| 4,954,083 A | 9/1990 | Leff et al. |
| 5,031,937 A | 7/1991 | Nellhaus |
| 5,127,756 A | 7/1992 | Lumm |
| 5,169,342 A | 12/1992 | Steele et al. |
| 5,226,163 A * | 7/1993 | Karsh et al. ................. 707/200 |
| 5,252,075 A | 10/1993 | Heng |
| 5,321,800 A | 6/1994 | Lesser |

(Continued)

*Primary Examiner*—Kristine Kincaid
*Assistant Examiner*—Sajeda Muhebbullah
(74) *Attorney, Agent, or Firm*—Senniger Powers (57) ABSTRACT

A system and method for graphically indicating patient information. The invention includes a representative image of the patient with icons to indicate or inform a health care worker of the condition of the patient. Each icon in a set of icons represents a condition available for use in describing the condition of a particular patient. Each icon is located at a predetermined position of the image in each implementation of the invention. After a user creates an image with icons selected for a particular patient, a fixed representation of the image is created. The fixed representation of the image (e.g., on a sheet of paper) is placed proximal to the patient (e.g., bedside) for visual conveyance of the patient's condition.

30 Claims, 3 Drawing Sheets

U.S. PATENT DOCUMENTS

| | | |
|---|---|---|
| 5,331,549 A | 7/1994 | Crawford, Jr. |
| 5,498,034 A | 3/1996 | Ford |
| 5,533,902 A | 7/1996 | Miller |
| 5,580,254 A | 12/1996 | Ramsey |
| 5,720,502 A * | 2/1998 | Cain ........................... 283/115 |
| 5,792,047 A | 8/1998 | Coggins |
| 5,826,237 A * | 10/1998 | Macrae et al. ................. 705/2 |
| 5,827,103 A | 10/1998 | Carter |
| 5,890,905 A | 4/1999 | Bergman |
| 5,924,074 A * | 7/1999 | Evans ........................... 705/3 |
| 5,960,403 A * | 9/1999 | Brown ........................... 705/2 |
| 5,970,499 A * | 10/1999 | Smith et al. .............. 707/104.1 |
| 5,984,368 A | 11/1999 | Cain |
| 6,032,119 A * | 2/2000 | Brown et al. ................... 705/2 |
| 6,056,549 A | 5/2000 | Fletcher |
| 6,314,405 B1 * | 11/2001 | Richardson .................... 705/3 |

* cited by examiner

METHOD OF GRAPHICALLY INDICATING PATIENT INFORMATION

TECHNICAL FIELD

This invention generally relates to systems and methods for conveying information about a patient in a nursing home or hospital using charts or illustrations and, in particular, a system and method for graphically indicating patient information using icons displayed on an image representative of the patient.

BACKGROUND OF THE INVENTION

Systems exist for communicating patient information to nursing home or hospital health care workers to assist in the care of the patient. Such information includes whether the patient is combative, hard-of-hearing, visually impaired, etc. Such systems convey this patient information by placing symbols on a representation of the specific patient, such as a photograph of the patient's face. However, there is a need for a system which conveys patient information more specifically by associating the patient information with a specific, applicable part of the patient's body in a manner easily recognized by a trained health care worker. For example, left leg weakness would be indicated by a specific symbol placed on top of the left leg of an image representing the patient.

Existing systems for communicating patient information include pictorial symbols or icons movable by the health care workers and anyone else who visits the patient. There is a need for a system which conveys patient information in a fixed representation generally unalterable by persons other than the health care workers.

The invention described below addresses these and other disadvantages.

SUMMARY OF THE INVENTION

The invention includes a system and method for graphically indicating patient information. The invention includes an image representing the patient with icons to indicate or inform a health care worker of the condition of the patient. Patients include residents of a long-term care facility such as a nursing home, patients undergoing rehabilitation, patients being treated at a hospital, or the like. Each icon selected from a set of icons represents a condition available for use in describing the condition of a particular patient. Each selected icon is located at a predetermined position of the image in each implementation of the invention. After a user creates an image representing a particular patient, a fixed representation of the image is created. The fixed representation of the image (e.g., on a sheet of paper) is placed proximal to the patient (e.g., bedside) for visual conveyance of the patient's condition. The icons in the fixed representation of the image can only be altered by accessing the system of the invention.

It is an object of this invention to provide a system which conveys patient information by visually associating the patient information with a specific part of the patient's body.

It is an object of this invention to provide a system which conveys patient information in a manner such that the patient information is unalterable by persons other than an administrator or other coordinator in charge of the system.

It is an object of this invention to provide a tool for health care workers that promotes worker safety and reduces workman's compensation claims.

It is another object of this invention to alert health care workers to the specialized care required for each patient by use of a picture graphic.

It is another object of this invention to meet Occupational Safety & Health Administration standards and avoid the possibility of a fine.

It is another object of this invention to meet United States Department of Aging recommendations on a patient's right to privacy.

It is another object of this invention to ensure the safety of patients and employees in health care facilities.

It is another object of this invention to provide an ergonomic tool for use throughout a health care facility.

It is also an object of the invention to present sensitive or confidential patient information in a manner that is not readily recognized by an untrained individual.

In accordance with one aspect of the invention, a method graphically indicates patient information. The method includes the steps of defining one or more conditions of a patient, selecting an icon corresponding to each of the defined conditions, and creating a fixed image wherein each of the selected icons is located at a predetermined position of the image.

In accordance with another aspect of the invention, a system graphically indicates information about a patient. The patient has one or more defined conditions selected from a set of available conditions. The system includes one or more icons, an image, and a creation component. Each of the icons corresponds to at least one of the available conditions. The image has a predetermined position for each of the icons. The creation component creates a fixed representation of the image with selected icons. Each of the selected icons corresponds to the defined conditions of the patient.

In accordance with another aspect of the invention, in a computer system having a graphical user interface including a display and a user interface selection device, a method provides and selects from a toolbar on the display. The method includes the steps of allowing a user to select with the user interface selection device one or more icons from the toolbar and displaying each of the selected icons on an image representative of the patient. Each of the icons corresponds to a condition of a patient.

In accordance with another aspect of the invention, a system graphically indicates patient information. The system includes means for defining one or more conditions of a patient, means for selecting an icon corresponding to each of the defined conditions, and means for creating a fixed image wherein each of the selected icons is located at a predetermined position of the image.

Alternatively, the invention may comprise various other methods and apparatuses.

DETAILED DESCRIPTION OF THE INVENTION

Figure 1:
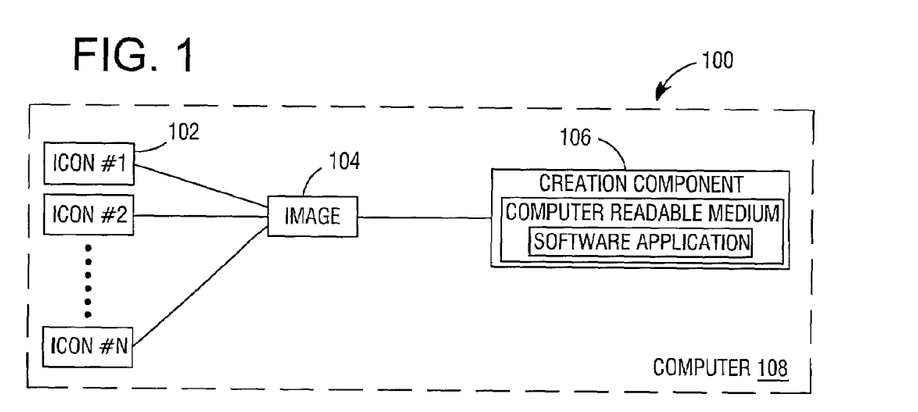
FIG. 1 is a block diagram of one embodiment of the method and system of the invention illustrating the main components of the invention.

Referring now to the drawings, FIG. 1 illustrates a patient information system 100 in block diagram form. The invention preferably includes icons 102, an image 104, and a creation component 106, all implemented on a computer 108. In general, the invention relates to a visual form of communication using the icons 102 on the image 104 which at a glance provides a health care worker with specific instructions for a patient. For example, the invention tells a health care worker how to care for a patient. At the same time, the system 100 promotes the safety of the worker and the patient, and provides privacy and confidentiality for the patient. System 100 is generally confidential because only the workers will understand what the icons 102 on image 104 reveal about the patient. The worker no longer has to stop caring for the patient to look up patient information or ask a co-worker about basic care instructions for the patient. For example, the worker will know just by looking over the patient's bed whether or not to use a lift or get another person to help when removing the patient from the bed. As such, system 100 is an ergonomic tool aimed at, but not limited to, health care workers. System 100 is also designed to comply with ergonomic standards acts and privacy acts.

As described in detail below, the patient has one or more defined conditions selected from a set of available conditions. Each of the icons 102 corresponds to at least one of the available conditions. In FIG. 1, the exemplary number of icons 102 is N, where N is a positive integer. Icon #1, icon #2, and icon #N are representative of the available icons 102. These icons 102 can be displayed on the image 104. Image 104 has a predetermined position for each of the icons 102 according to the invention. The creation component 106 creates a fixed representation of image 104 with selected icons 102. Creation component 106 preferably includes a computer readable medium storing a software application which executes to perform the functions of the creation component.

Exemplary images used to represent the patient, such as image 104, include, but are not limited to, a teddy bear, a human likeness, a likeness of a particular patient, any animal (e.g., a kangaroo), a robot, or any animated object with two arms, two legs, a torso, and a head. The image 104 can be any color, shape, or size. Where the health care facility is a hospital, for example, there can be a specialized image for each department in the hospital. Other applications of the invention include communicating care plan goals and producing an image which serves as a material data sheet (MDS). As part of the MDS, the produced image can be submitted to the state on a quarterly basis or as an annual assessment by an MDS coordinator. Those skilled in the art will note that the invention is applicable to describe the condition of any object (human, animal or otherwise), and that the term "patient" is used herein in a non-limiting way. Further, in one embodiment, the invention is applicable in health care facilities including, for example, a long-term care facility, a rehabilitation center, a dietary department, or a hospital. A long-term care facility includes a nursing home. The health care facilities can use an image to graphically represent any information which traditionally appears as text.

One advantage of providing readily available patient care information is the reduction in worker back, shoulder, wrist, neck, and joint injuries caused by improper patient handling. The invention is applicable to about two-thirds of all health care worker patient handling injuries: approximately one-third of which are musculoskeletal disorders (MSD), and another one-third of which are "violence in the work place" incidents between worker and patient. Therefore, the invention should reduce a significant number of health care worker injuries. The remaining one-third of worker injuries are attributable to miscellaneous causes (slipped on water, bee sting, etc.). The invention tells the worker how to properly care for the patient and, thus, can reduce the money spent on worker's compensation injuries.

A mismatch between the physical requirements of the job and the physical capacity of the worker is a leading cause of MSDs. For example, workers who repeat the same motion throughout their work day, who must do the work in an awkward position, who must use a great deal of force to perform their job, who must repeatedly lift heavy objects or who face a combination of these risk factors are most likely to develop MSDs. MSDs are injuries and disorders of the muscles, nerves, cartilage, spinal discs, and joint injuries (e.g., carpal tunnel syndrome, tendinitis, sciatica, herniated discs, low back pain, shoulder pain, and neck pain). They do not include slips, trips, falls, or similar accidents.

Figure 2:
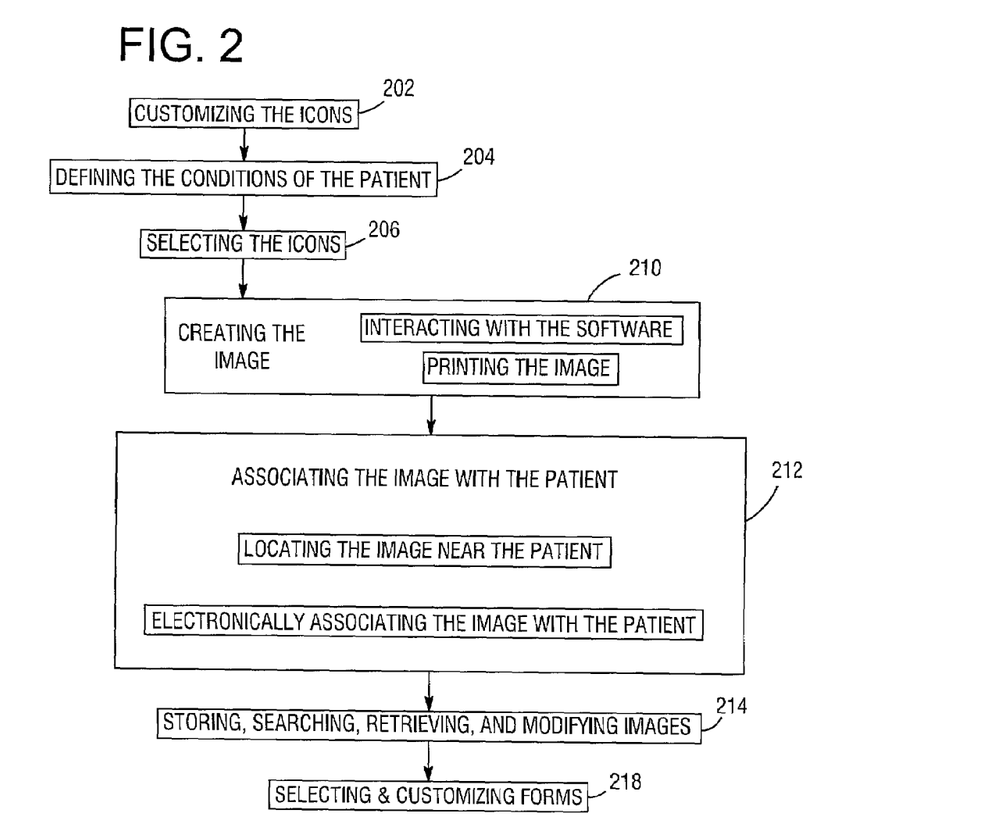
FIG. 2 is a flow chart of one embodiment of the method and system of the invention illustrating operation of the invention.

Referring now to FIG. 2, a flow chart illustrates operation of system 100 according to a preferred embodiment of the invention. Beginning at 202, a standard set of conditions are available in the invention (see FIG. 3). In addition, a user of the invention, such as a health care worker or other authorized person, can customize at least one icon 102 to represent a health condition not included in the standard set. For example, in one embodiment, there are four icons for customization by the user: a lightning bolt, a five-pointed star, a rocking horse, and a flower. Further, instead of using the standard set of icons, the user can create and save custom icons for each condition.

In operation of the invention, one or more conditions of a patient are defined at 204, such as by a physician or other health care worker. The user selects the particular icon 102 corresponding to each of the defined conditions. As the user executes creation component 106 to select each icon at 206, the selected icon appears on image 104 at a predetermined position on the image. The user can also de-select icons 102 to remove them from the image 104. In another embodiment, the user selects an icon 102 and "drags" the icon 102 to the predetermined position for that icon 102. After the user completes the image 104, the user fixes the image so that each of the selected icons 102 is located at its respective predetermined position of the image 104. In one embodiment, creating the image 104 occurs at 210 and includes interacting with the software of creation component 106 and printing the image 104. The software moves each of the selected icons 102 to its predetermined position on the image 104. Additionally, the software generates an electronic representation of image. The software prints image 104 with the selected icons 102 in their respective, predetermined positions on the image. The icons 102 in the fixed image 104 can only be altered by accessing the system 100 of the invention. For example, to change the icons 102 on an image for a particular patient, the user accesses system 100 to select or de-select icons 102 and to print another fixed image 104. In this manner, non-users, such as other patients, or family members of patients, cannot add, delete, or move icons 102 on the fixed images 104.

In one embodiment, image 104 is proximally associated with the patient at 212. For example, image 104 can be located at the patient's bedside. In this manner, the user is alerted to the condition of the patient via the image 104. Alternatively, an electronic representation of the image 104 is associated with the patient. For example, image 104 may be displayed on a computer monitor near the patient.

The image 104 with the selected icons 102 is preferably stored in a computer readable medium. Referring further to FIG. 2, a plurality of images for different patients are stored in the computer readable medium and, at 214, the images can be searched, retrieved, and modified. The user can search the stored images based on, for example, an identification number, name, or condition associated with the patient. When the conditions of a particular patient change, the stored image 104 associated with the particular patient can be modified. For example, the modification may occur quarterly on demand by the user. In one embodiment, a modification reminder is sent to the user once every quarter (e.g., as an electronic mail transmission). Also, an archive of original and modified images is preferably maintained to provide a patient history for the user.

It is anticipated that those skilled in the art will note that any combination of the steps in FIG. 2 may be performed by computer-executable instructions on one or more computer readable media.

In one embodiment, the invention is operable in computer system 108 having a graphical user interface including a display and a user interface selection device. The user interface selection device allows the user to interact with the computer system 108. For example, the user interface selection device may be a mouse, keyboard, or touch screen. Computer system 108 provides a toolbar on the display from which the user performs various functions. In particular, via computer system 108, the user selects with the user interface selection device one or more of the icons 102 from the toolbar. Computer system 108 displays each of the selected icons 102 on the image 104 representative of the patient. Each of the selected icons 102 is displayed at a predefined position of the image 104. Via computer system 108, the user creates a fixed representation of image 104. The fixed representation of the image 104 is proximally associated with the patient. For example, the fixed representation may be a printout placed at the patient's bedside or a graphic displayed on a computer monitor placed near the patient. In one embodiment, at least one of the icons 102 is linked to at least one other icon 102 such that selecting the one icon from the toolbar automatically selects the other icons. For example, the condition of combativeness typically requires that additional health care workers are needed to move the particular patient. As such, in one embodiment, as the user creates the image 104 for the particular patient, selecting the helmet icon also selects the butterfly icon.

Via the user interface selection device of the computer system, the user also selects and customizes various forms as shown at reference character 218 in FIG. 2. In an exemplary embodiment, the forms include an accident investigation report, an employee information test, an employee report of injury, an employee resident survey, a facility to-do list, an incident report, a patient information form, a resident handling ergonomics program, a resident handling program key and explanation, a resident handling program training outline, and at least one safety form. The user customizes the selected form(s) by inputting information relevant to the selected form. For example, the patient information form requires the patient's name, address, and telephone number. Each customized form is stored in a computer readable medium.

In one embodiment, a physical exam or other patient observance by a physician or other health care worker constitutes means for defining one or more conditions of the patient. A software application and a user interface selection device constitute means for selecting an icon corresponding to each of the defined conditions. A software application, printer, and a display constitute means for creating a fixed image wherein each of the selected icons is located at a predetermined position of the image. Further, the examples described above and examples described elsewhere herein constitute means for defining one or more conditions of the patient, means for selecting an icon corresponding to each of the defined conditions, and means for creating a fixed image wherein each of the selected icons is located at a predetermined position of the image.

Figure 3:
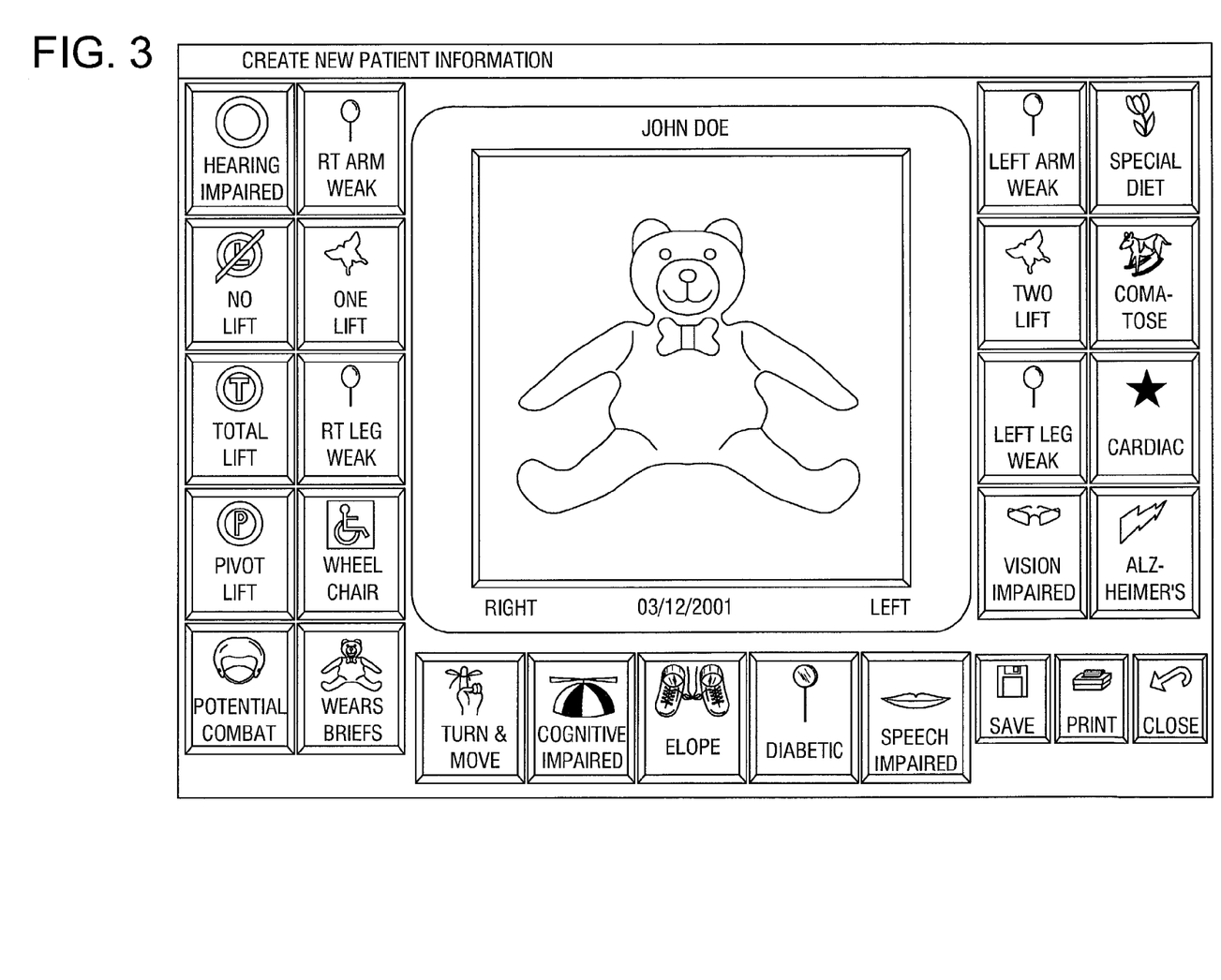
FIG. 3 is an exemplary embodiment of the method and system of the invention illustrating a user interface for creating the image.

Referring next to FIG. 3, an exemplary embodiment of the invention illustrates a user interface for creating the image 104. Those skilled in the art will note that exemplary embodiments of the invention can include icons, icons with descriptive text, or descriptive text without icons. In the exemplary embodiment of FIG. 3, the user interface includes icons with descriptive text. The image in FIG. 3 portrays a teddy bear wearing a bow-tie, where the color of the bow-tie indicates the gender of the patient. For example, a blue bow-tie indicates a male patient, and a pink bow-tie indicates a female patient. A rectangular frame surrounds the bear, with a name of the patient above the frame and a date below the frame. In this exemplary embodiment, the name of the patient is "John Doe" and the date is "Mar. 12, 2001." The words "right" and "left" appear in the lower left and right corners of the frame, respectively, to indicate the anatomical location on the patient's body. Icons appear along the left side of the frame in two columns and five rows, entitled "hearing impaired," "rt arm weak," "no lift," "one lift," "total lift," "rt leg weak," "pivot lift," "wheelchair bound," "potential combat," and "wears briefs." Icons also appear along the right side of the frame in two columns and four rows, entitled "left arm weak," "special diet," "two lift," "comatose," "left leg weak," "cardiac," "vision impaired," and "Alzheimer's." In this exemplary interface, five icons appear below the frame, entitled "turn and move," "cognitive impaired," "elope," "diabetic," and "speech impaired." Three small icons appear in the lower right corner of the frame, entitled "save," "print," and "close."

The icons 102 shown in the exemplary embodiment of FIG. 3 are next discussed in detail as part of the following examples. Each of the icons 102 may convey a basic health care plan goal at the discretion of the health care facility. A care plan is an individualized plan of care for each patient. The care plan covers problems, goals, and approaches to achieving the goals. The bow-tie conveys gender with the center of the bow-tie holding any other symbol. The bow-tie can be a ribbon, necklace or anything going around a neck in the image. A pink bow-tie indicates that the patient is female, a blue bow-tie indicates that the patient is male. The bow-tie can be any color, shape, or size. In a preferred embodiment, the center of the bow-tie holds a wheelchair. The wheelchair or any symbol that indicates work or disability is located in the center of the bow-tie even if the patient is not wheelchair bound at all times.

Eye glasses, or any object orbiting the eyes on the image including sun glasses, safety glasses, or bifocals convey that the patient is vision impaired or possibly blind. This reminds the worker to make sure the patient has glasses on or if the glasses are lost, assist the patient in locating items and generally moving about. For example, when eating a meal, the worker would tell the patient that the meat is at 12 o'clock, the vegetable at 3 o'clock, the mashed potatoes at 6 o'clock, and the dessert at 9 o'clock, analogous to the hour hand positions on a clock face.

The beanie hat, or any hat, object, bonnet, etc. on the bear's or object's head (other than a helmet), helps prevent cognitive impairment, for example. This is also a tool that helps prevent work place violence between worker and patient, which is an Occupational Safety and Health Administration (OSHA) issue and Department Of Aging issue. The baby bear conveys to the worker that the patient suffers from incontinence, wears briefs (diapers), or uses underpads. In one embodiment, the baby bear is located on the right side of the arm in the image. This icon tells the worker to check the patient frequently for incontinence. This icon also tells the worker that the patient will need cleaning care, which typically means physically cleaning the patient with peri-wash or soap and water.

The balloons preferably indicate weakness in the patient's extremities. The balloons or any object will be on the tip of the limb that is weak or paralyzed. The weak limbs may be any of the four limbs (two arms and two legs). This tells the worker where the patient is weak. The balloons also instruct the worker to check for splints for the patient. The balloons alert the worker that the patient may not have feeling in that limb. For example, extreme cold or heat could hurt the limb, and the patient would not be aware of the injury. The balloons convey ergonomics and work place violence prevention.

The helmet, shield, or other protective gear conveys that the patient has the potential to become combative or potentially violent in this example. The helmet is located on the left side of the image. This also automatically conveys that the patient requires a two person assist. The helmet also alerts the worker to use caution when approaching the patient so as to not agitate the patient. The helmet also alerts the worker to make sure they care for the patient in a non-confrontational manner.

The shoes, boots, sandals, high heels, etc. indicate the potential for the patient to elope. This also tells the worker to check regularly on the whereabouts of the patient. The worker can check a "wander guard" if applicable. This icon also conveys a work place violence prevention issue. The butterfly or any object on the shoulder of the image conveys the number of workers needed to lift or assist with that patient. The finger with string indicates that the patient needs to be turned and repositioned. The empty circle or other empty shape indicates hearing impairment. This alerts the worker to assist the patient with the hearing aid, to speak up, and to carefully communicate with the patient so as to not agitate the patient. A circle with the letter "L" in its center and a line crossing the letter and circle in a diagonal fashion indicates that no lift is required (the patient is independent). A circle with the letter "T" in its center indicates that a total lift is required. A circle with the letter "P" in its center indicates that a pivot lift is required for the patient. The lollipop indicates that the patient is diabetic. This conveys to the worker to double-check the diet of the patient. This icon lets the worker know if the patient can have sweets, etc. The red lips indicate speech impairment. The lips indicate that the patient cannot talk, cannot understand, or mumbles. In the exemplary embodiment of FIG. 3, four customized icons include a flower that indicates a special diet, a rocking horse to indicate that the patient is comatose, a five-pointed star to indicate that the patient suffers cardiac problems, and a lightning bolt to indicate that the patient has Alzheimer's disease.

The information provided by the following icons 102 will help reduce work place violence: the butterfly or any object on the shoulders of the image, the red lips or anything on the mouth of the image, the shoes (or anything that indicates elopement), the helmet, the beanie cap or anything on the head of the image, the empty circle. The following symbols will help reduce MSDs: the butterfly, the wheelchair, the balloons, the finger with string, any of the circles with or without letters.

Figure 4:
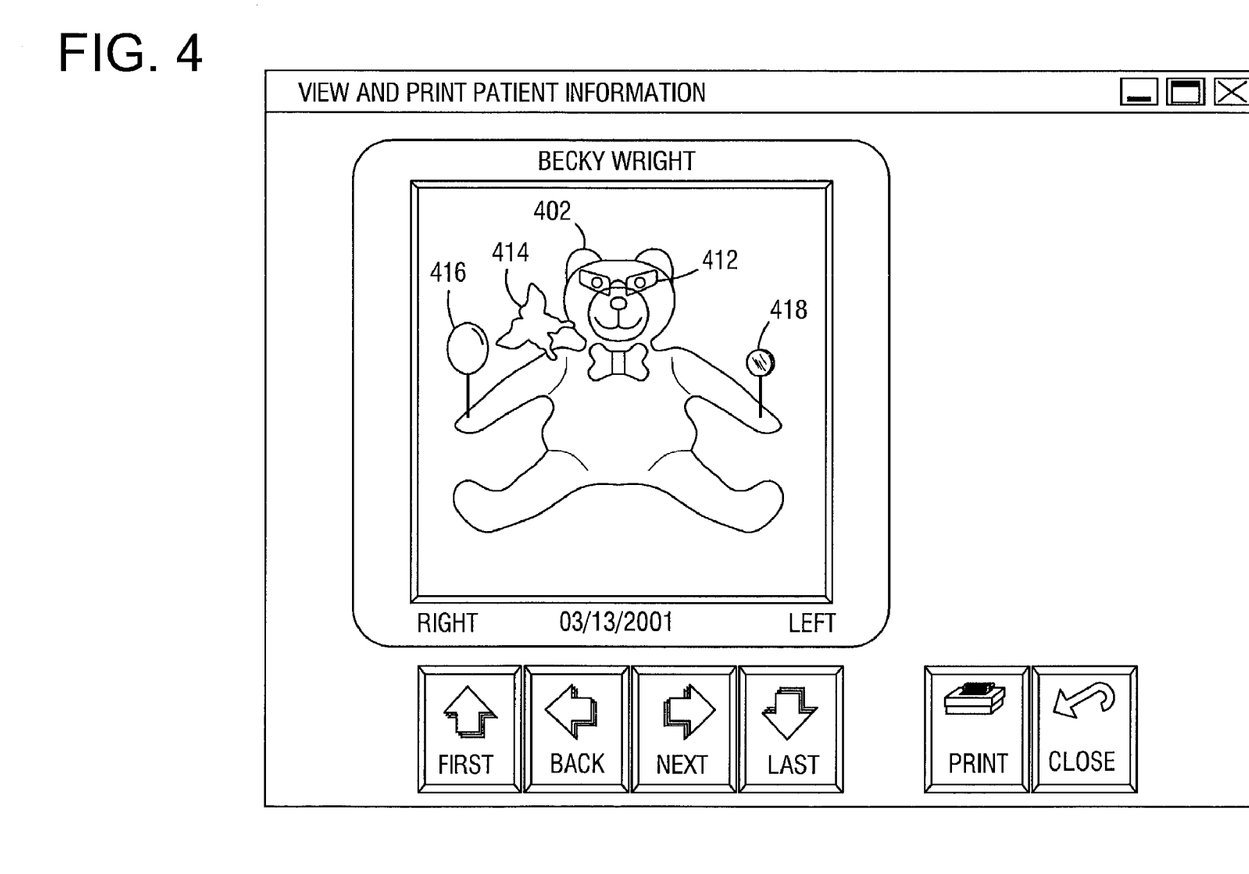
FIG. 4 is an exemplary embodiment of the method and system of the invention illustrating a user interface for viewing and printing patient information.

Referring next to FIG. 4, an exemplary embodiment of the invention illustrates a user interface for viewing and printing patient information. A teddy bear 402 with a bow-tie is the exemplary image 104 in this embodiment. The name "Becky Wright" appears above a rectangular frame around the bear 402 indicating that this image represents the condition of a patient named Becky Wright. The date "Mar. 13, 2001" appears below the frame to indicate the date the image 104 was created. The words "right" and "left" appear in the lower left and right corners of the frame, respectively, to indicate the anatomical location on the patient's body. The bear 402 has the following icons 102 to indicate the patient conditions selected during creation of the image 104: glasses 412, a butterfly 414 on the right arm, a balloon 416 on the right hand, and a lollipop 418 on the left hand. In this example, the patient Becky Wright has the following conditions, respective to the list of icons above: vision impairment, one additional person needed to help lift, right arm weakness, and diabetes. Arrows below the frame indicate "first," "previous," "next," and "last" for selecting the first, previous, next, and last available images. Icons entitled "print" and "cancel and close" appear to the lower right of the frame.

The icons 102 preferably use a standard set of graphics which are all used in the same way in each implementation of the invention. Icons 102 will be placed in the same location on each image 104. Health care facilities are encouraged to maintain change the meaning of the standard icons to prevent confusion about patient care from occurring as workers change jobs. Any worker changing jobs will know the system so the worker will immediately be able to recognize patient conditions from job to job. Any nurse, CNA, or person working in a nursing home or long term care facility anywhere in the country can look at the image 104 and know the patient and know what it is, what it means, and how to care for the patient. This system 100 will prevent new workers or agency help from misplacement of the patient information sheet. The system 100 will also protect patient safety and worker safety.

The system 100 of the invention has many benefits. The system 100 reduces the time required to complete certified nursing assistant (CNA) assignments by eliminating the need to type, hand write, or answer the same questions about the patient information several times. The system 100 also saves the CNA time by reducing the questions that other workers may ask of the CNA regarding care of the patient. The system 100 provides safety to the patient as well as the worker. The nurse will not spend time cutting up assignment or room numbers because part of assignment two is on the third sheet and part of assignment four is on the third or fifth sheet. The system 100 allows the nurse to avoid updating handwritten assignments. Updating the handwritten assignments would normally require whiting-out old patient's names and putting new patient names and data on the sheet and making photocopies weekly.

The system 100 also visually communicates health care goals of the patient to the worker. For example, if the image 104 includes the baby bear icon 102, the patient associated with the image 104 is incontinent. With this information, the worker knows that the patient needs particular care after each incontinence episode. Further, the worker is also aware of one of the health care goals of the patient: to be clean, dry, free of odors, and free of skin breakdown. The health care facility can implement health care goals to be associated with a specific icon 102. The workers can memorize the icons 102 first, then the health care goals if implemented. It is a requirement by the Department Of Aging for all CNAs to know at least one or two health care goals. The system 100 serves as a significant portion of a report to the CNAs.

In one embodiment, system 100 will be available for facility use on a compact disc (CD) on computer 108. Each health care facility will have its own CD to produce the image 104 for each patient. The image 104 can be assembled and placed above the patient's bed in just a few minutes after the patient is admitted after initial assessment. The CD also contains instructions and printable forms. The system 100 is simple to use with by clicking, a minimal typing (including the patient's name), and then printing the image 104. In an alternative embodiment, the system 100 is provided to health care workers via a global computer network, such as the Internet. In this embodiment, the system 100 is available as software downloadable over a network to the user's computer for execution. In yet another embodiment, software associated with the system 100 executes primarily on a central server accessible by a network via a computer operated by the user. For example, the user can remotely interact with the system 100 via a web browser to create an image and then locally print the image using the browser software. In this embodiment, the user does not need to possess and install the software locally.

A database associated with computer 108 stores current images 104, the archived images, and other patient and worker data. For each patient and worker, the database stores data including a first and last name, an identification number, and a number of incidents relating to the worker or patient. By storing such information, the database facilitates tracking and trend analysis of incidents. In one embodiment, the database is local to computer 108 operated by the user. In another embodiment, the database is remotely accessible by computer 108 operated by the user. In this embodiment, the database may be located within a computer center at the health care facility, or located off-site from the health care facility and accessible via a network. For example, the database may be maintained at an off-site location by technicians not associated with the health care facility. Additionally, the software application may be accessible by users at computer terminals located throughout the health care facility while the database is centrally located and accessible by a network. In another embodiment, the images in the database can be exported to other databases.

While the icons 102 described herein illustrate one embodiment of the invention, it is contemplated that the invention is at least applicable in other embodiments where each icon 102 in a particular embodiment consistently represents the same condition for all images 104 created in the particular embodiment. Further, the location of each icon 102 on each image 104 created in a particular embodiment is consistent for all images 104 created in the particular embodiment.

Those skilled in the art will note that the invention is operational with numerous general purpose or special purpose computing system environments or configurations. A computer for use in the invention typically has at least some form of computer readable media. Computer readable media, which include both volatile and nonvolatile media, removable and non-removable media, may be any available medium that can be accessed by the computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of the any of the above are also included within the scope of computer readable media.

The computer may also include other removable/non-removable, volatile/nonvolatile computer storage media. For example, the computer storage media include a hard disk drive that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD-ROM or other optical media.

The invention may be described in the general context of computer-executable instructions, such as program modules, executed by one or more computers or other devices. Generally, program modules include, but are not limited to, routines, programs, objects, components, and data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

The invention claimed is:

1. A method of graphically indicating patient information in a confidential manner, said method comprising the steps of:

relating each of a plurality of icons to a predetermined position in a fixed image associated with a patient;

receiving information identifying one or more conditions of the patient, each of the identified conditions of the patient being associated with a location on the body of the patient;

selecting at least one icon from the plurality of icons, said selected icon corresponding to at least one of the identified conditions of the patient; and creating the fixed image, said fixed image including the selected icon located at the predetermined position related thereto in the fixed image, wherein the predetermined position related to the selected icon in the fixed image is independent of the location, on the body of the patient, associated with the identified condition of the patient corresponding to the selected icon to protect the privacy of the patient.

2. The method of claim 1, further comprising the step of proximally associating the image with the patient.

3. The method of claim 1, wherein the conditions are selected from the group consisting of: hearing impairment, right arm weakness, left arm weakness, special diet, no lift, one person lift, two person lift, comatose, total lift, right leg weakness, left leg weakness, cardiac, pivot lift, wheelchair bound, vision impairment, Alzheimer's, potentially combative, incontinent, turn and reposition, cognitive impairment, potential to elope, diabetic, and speech impairment.

4. The method of claim 1, further comprising the step of associating an electronic representation of the image with the patient.

5. The method of claim 1, wherein the step of creating the fixed image includes generating an electronic representation of the image and moving each of the selected icons to its predetermined position on the image.

6. The method of claim 5, further comprising the step of printing the image with the selected icons in their respective, predetermined positions on the image.

7. The method of claim 5, further comprising the step of executing a computer program for automatically positioning the selected icons in their respective, predetermined positions on the image.

8. The method of claim 5, further comprising the step of storing the image with the selected icons in a computer readable medium.

9. The method of claim 8, wherein a plurality of images for different patients are stored in the computer readable medium and further comprising the step of searching for a stored image based on a name associated with the patient.

10. The method of claim 8, further comprising the step of modifying a stored image associated with a particular patient when the conditions of the particular patient change.

11. The method of claim 1, further comprising the step of customizing at least one icon to represent a specific condition.

12. The method of claim 11, further comprising the step of maintaining an archive of original and modified images.

13. The method of claim 1, further comprising the step of alerting a health care worker to the at least one of the identified conditions of the patient via the image.

14. One or more computer readable media having computer-executable instructions for performing the method recited in claim 1.

15. The method of claim 1, further comprising displaying the fixed image.

16. The method of claim 1, further comprising:
displaying the fixed image proximal to the patient to confidentially communicate the at least one of the identified conditions of the patient to a person with knowledge of the relationship between each of the plurality of icons and the predetermined position.

17. A system for graphically indicating information about a patient in a confidential manner, wherein the patient has one or more conditions identified from a set of available conditions, said system comprising:

an image associated with the patient;

one or more icons, each of said one or more icons corresponding to at least one of the available conditions, and each of said one or more icons being related to a predetermined position in the image; and a creation component for creating a fixed representation of the image with selected icons, each of the selected icons corresponding to at least one of the identified conditions of the patient, each of the identified conditions of the patient being associated with a location on the body of the patient, each of the selected icons being located at the predetermined position related thereto, and wherein the predetermined position related to each of the selected icons in the fixed image is independent of the location, on the body of the patient, associated with the identified condition of the patient corresponding to the selected icon to protect the privacy of the patient.

18. The system of claim 17, wherein the creation component comprises a software application stored on a computer readable medium.

19. The system of claim 18, wherein the software application includes computer-executable instructions which, when executed, place each of the selected icons at the predetermined position related thereto on the image.

20. The system of claim 18, wherein the software application includes computer-executable instructions which, when executed, electronically associate the fixed representation of the image with the patient.

21. The system of claim 18, wherein the software application includes computer-executable instructions which, when executed, print the fixed representation of the image with the selected icons in the predetermined positions on the image for placement proximal to the patient.

22. In a computer system having a graphical user interface including a display and a user interface selection device, a method of providing and selecting from a menu on the display, comprising the steps of:

allowing a user to select with the user interface selection device one or more icons from the menu, each of said one or more icons corresponding to a condition of a patient and being assigned to a predetermined position in an image representative of the patient, said condition of the patient being associated with a location on the body of the patient; and displaying each of the said one or more icons on the image on the display, each of said one or more icons being displayed at the predetermined position assigned thereto in the image, wherein the predetermined position assigned to the icon in the fixed image is independent of the location, on the body of the patient, associated with the identified condition of the patient corresponding to the icon to protect the privacy of the patient.

23. The method of claim 22, further comprising the step of allowing the user to create a fixed representation of the image.

24. The method of claim 23, further comprising the step of allowing the user to proximally associate the fixed representation of the image with the patient.

25. The method of claim 22, wherein at least one of the icons is linked to at least one other icon such that selecting the at least one icon from the menu automatically selects the at least one other icon.

26. The method of claim 22, further comprising the step of allowing the user to select with the user interface selection device a form from the group consisting of: an accident investigation report, an employee information test, an employee report of injury, an employee resident survey, a facility to do list, an incident report, a patient information form, a resident handling ergonomics program, a resident handling program key and explanation, a resident handling program training outline, and at least one safety form.

27. The method of claim 26, further comprising the step of allowing the user to customize the selected form by inputting information relevant to the selected form.

28. The method of claim 27, further comprising the step of storing each customized form in a computer readable medium.

29. One or more computer readable media having computer-executable instructions for performing the method recited in claim 22.

30. A system for graphically indicating patient information in a confidential manner, said system comprising:

means for relating each of a plurality of icons to a predetermined position in a fixed image associated with a patient and receiving information identifying one or more conditions of the patient, each of the identified conditions of the patient being associated with a location on the body of the patient;

means for selecting a first icon and a second icon from the plurality of icons, each of said first icon and said second icon corresponding to at least one of the identified conditions of the patient; and means for creating the fixed image, said fixed image including the first icon located at the predetermined position related thereto in the fixed image, said fixed image including the second icon located at the predetermined position related thereto in the fixed image, wherein the predetermined position related to the first icon in the fixed image is independent of the location, on the body of the patient, associated with the identified condition of the patient corresponding to the first icon, and the wherein the predetermined position related to the second icon in the fixed image indicates the location, on the body of the patient, associated with the identified condition of the patient corresponding to the second icon.

* * * * *

UNITED STATES PATENT AND TRADEMARK OFFICE
CERTIFICATE OF CORRECTION

| | |
|---|---|
| PATENT NO. | : 7,107,547 B2 |
| APPLICATION NO. | : 09/870373 |
| DATED | : September 12, 2006 |
| INVENTOR(S) | : Cule et al. |

It is certified that error appears in the above-identified patent and that said Letters Patent is hereby corrected as shown below:

Column 11, claim 1, line 2: "corresponding" should read -- having a correspondence --.

Column 11, claim 1, line 3: "patient; and" should read -- patient, wherein the correspondence is recognizable in the fixed image only by a person having prior knowledge of the correspondence; and --.

Column 11, claim 1, line 8: "independent of" should read -- unrelated to --.

Column 11, claim 14, line 55: "One" should read -- The method of claim 1, wherein one --.

Column 11, claim 14, line 57: "recited in claim 1" should be deleted.

Column 12, claim 17, line 10: "corresponding" should read -- having a correspondence --.

Column 12, claim 17, line 11: "patient, each" should read -- patient, wherein the correspondence is recognizable in the fixed representation of the image only by a person having prior knowledge of the correspondence, each --.

Column 12, claim 17, lines 16-17: "independent of" should read -- unrelated to --.

Column 12, claim 22, line 44: "corresponding" should read -- having a correspondence --.

Column 12, claim 22, line 46: "patient, said" should read -- patient, wherein the correspondence is recognizable in the image only by a person having prior knowledge of the correspondence, said --.

Column 12, claim 22, lines 53-54: "independent of" should read -- unrelated to --.

Column 13, claim 29, line 16: "One" should read -- The method of claim 22, wherein one --.

Column 13, claim 29, line 18: "recited in claim 22" should be deleted.

Column 14, claim 30, line 6: "corresponding" should read -- having a correspondence --.

UNITED STATES PATENT AND TRADEMARK OFFICE
CERTIFICATE OF CORRECTION

PATENT NO. : 7,107,547 B2
APPLICATION NO. : 09/870373
DATED : September 12, 2006
INVENTOR(S) : Cule et al.

It is certified that error appears in the above-identified patent and that said Letters Patent is hereby corrected as shown below:

Column 14, claim 30, line 7: "patient; and" should read -- patient, wherein the correspondence is recognizable in the fixed image only by a person having prior knowledge of the correspondence; and --.

Column 14, claim 30, line 14: "independent of" should read -- unrelated to --.

Column 14, claim 30, line 17: "and the wherein" should read -- and wherein --.

Signed and Sealed this

Eighteenth Day of December, 2007

JON W. DUDAS
*Director of the United States Patent and Trademark Office*